United States Patent
Hagiwara et al.

(10) Patent No.: US 11,155,775 B2
(45) Date of Patent: Oct. 26, 2021

(54) CELL CULTURE VESSEL AND SAMPLE CELL FOR OBSERVATION USE

(71) Applicants: OSAKA PREFECTURE UNIVERSITY PUBLIC CORPORATION, Sakai (JP); NATIONAL UNIVERSITY CORPORATION KYUSHU INSTITUTE OF TECHNOLOGY, Kitakyushu (JP)

(72) Inventors: Masaya Hagiwara, Sakai (JP); Tomohiro Kawahara, Kitakyushu (JP)

(73) Assignees: OSAKA PREFECTURE UNIVERSITY PUBLIC CORPORATION, Osaka (JP); NATIONAL UNIVERSITY CORPORATION KYUSHU INSTITUTE OF TECHNOLOGY, Fukuoka (JP)

( * ) Notice: Subject to any disclaimer, the term of this patent is extended or adjusted under 35 U.S.C. 154(b) by 676 days.

(21) Appl. No.: 15/779,951

(22) PCT Filed: Nov. 7, 2016

(86) PCT No.: PCT/JP2016/082979
§ 371 (c)(1),
(2) Date: May 30, 2018

(87) PCT Pub. No.: WO2017/094451
PCT Pub. Date: Jun. 8, 2017

(65) Prior Publication Data
US 2019/0002812 A1 Jan. 3, 2019

(30) Foreign Application Priority Data
Dec. 4, 2015 (JP) .............................. JP2015-237526

(51) Int. Cl.
*C12M 1/00* (2006.01)
*C12M 1/12* (2006.01)

(52) U.S. Cl.
CPC ............ *C12M 23/22* (2013.01); *C12M 23/18* (2013.01); *C12M 25/14* (2013.01)

(58) Field of Classification Search
CPC ....... C12M 23/22; C12M 23/18; C12M 25/14
See application file for complete search history.

(56) References Cited

U.S. PATENT DOCUMENTS

2007/0003526 A1  1/2007  Hayashi
2013/0280807 A1* 10/2013 Takezawa .......... G01N 33/5008
435/397

(Continued)

FOREIGN PATENT DOCUMENTS

| JP | 2009-213716 A | 9/2009 |
| WO | 2004/084967 A1 | 10/2004 |
| WO | 2012/147878 A1 | 11/2012 |

OTHER PUBLICATIONS

Huisken, Jan, et al. "Optical Sectioning Deep Inside Live Embryos by Selective Plane Illumination Microscopy," Science, Aug. 13, 2004, vol. 305, pp. 1007-1009.

*Primary Examiner* — William H. Beisner
*Assistant Examiner* — Danielle B Henkel
(74) *Attorney, Agent, or Firm* — Stites & Harbison, PLLC; Jeffrey A. Haeberlin; James R. Hayne (57) ABSTRACT

The present invention provides a cell culture vessel or a sample cell for observation use that makes it possible to observe three-dimensionally-cultured cells from various angles. The cell culture vessel or the sample cell for observation use according to the present invention is characterized by being equipped with a culture gel in which a cell or cell tissue is embedded and a first vessel which encloses the culture gel, wherein a space in the first vessel is filled with (Continued)

the culture gel; and the first vessel has a light-permeable window made from a hydrogel.

8 Claims, 5 Drawing Sheets

(56) References Cited

U.S. PATENT DOCUMENTS

| | | |
|---|---|---|
| 2014/0113365 A1 | 4/2014 | Nagai et al. |
| 2015/0248949 A1* | 9/2015 | Bayley ................ G01N 27/416 |
| | | 174/258 |
| 2020/0017814 A1* | 1/2020 | Hagiwara ................ C12N 5/00 |
| 2020/0032186 A1* | 1/2020 | Hagiwara .............. C12M 23/22 |

* cited by examiner

CELL CULTURE VESSEL AND SAMPLE CELL FOR OBSERVATION USE

TECHNICAL FIELD

The present invention relates to a cell culture vessel and a sample cell for observation use, and relates particularly to the cell culture vessel suited for observing three-dimensionally-cultured cells.

BACKGROUND ART

Studies have been conducted on formation of blood vessel tissue, bronchial tissue, etc. by culturing cell tissue in three dimensions in a culture gel (see, for example, Patent Literatures 1 to 3). In these studies, the thick-layered culture gel is usually prepared in a dish or a well; and cells or cell tissue is embedded in this culture gel layer to culture the cell tissue. An observation means is to observe the cultured cell tissue from the lower side or the upper side of the culture gel layer by using an inverted microscope or an upright microscope. To obtain three-dimensional images of the cultured cell tissue, a laser microscope is used (see, for example, Non-Patent Literature 1).

CITATION LIST

Patent Literatures

PTL 1: Japanese Unexamined Patent Application Publication No. 2009-213716
PTL 2: WO 2004/084967 A
PTL 3: WO 2012/147878 A

Non-Patent Literature

NPL 1: HUISKEN, Jan, et al. Science. 305. 13 Aug. 2004. 1007-1009

SUMMARY OF INVENTION

Technical Problems

In the previous studies of the three-dimensional culture of the cell tissue, only bright-field images of the cell tissue can be obtained that is observed from its upper side or lower side; therefore, it is difficult to perceive a three-dimensional structure of the cell tissue only from the bright-field images. In a case where the cell tissue is thick in its height direction, it is difficult to observe the cell tissue because light cannot pass through some parts of the cell tissue where are high in cell density. The laser microscope also has a problem in observing the cell tissue such that it is difficult to carry out the live observation for a long time because a laser causes damage to the cell tissue. Also, the laser microscope is costly. Furthermore, the three-dimensional images obtained by the laser microscope have limitations in resolution in a z-axis direction.

In view of such circumstances, the present invention provides a cell culture vessel/a sample cell for observation use that makes it possible to observe three-dimensionally-cultured cells from various angles.

Solutions to Problems

The present invention provides a cell culture vessel characterized by being equipped with a culture gel in which a cell or cell tissue is embedded and a first vessel which encloses the culture gel, wherein a space in the first vessel is filled with the culture gel; and the first vessel has a light-permeable window made from a hydrogel.

The present invention also provides a sample cell for observation use characterized by being equipped with a culture gel in which a cell or cell tissue is embedded and a first vessel which encloses the culture gel, wherein a space in the first vessel is filled with the culture gel; and the first vessel has a light-permeable window made from a hydrogel.

The present invention also provides a cell culture vessel characterized by being equipped with a first vessel having an interior space to be filled with a culture gel in which a cell or cell tissue is embedded, wherein the first vessel has a light-permeable window made from a hydrogel.

Advantageous Effects of Invention

Since the cell culture vessel/the sample cell for observation use according to the present invention is equipped with the culture gel in which the cell or the cell tissue is embedded, the cell tissue can be cultured in three dimensions in the culture gel.

Since the cell culture vessel/the sample cell for observation use according to the present invention is equipped with the first vessel enclosing the culture gel, and the space in the first vessel is filled with the culture gel, the culture gel and the cell tissue can be confined in the first vessel; and the culture gel can be prevented from moving inside (or drifting in) the first vessel, and the cell tissue can be prevented from deviating from its relative position. This can prevent the relative position of the cell tissue from shifting and can allow the first vessel to rotate in a horizontal direction, a vertical direction, or an oblique direction.

Since the first vessel has the light-permeable window, the cell tissue inside the first vessel can be observed under the microscope or the like through the window. Since the cell tissue is prevented from deviating from its relative position while the first vessel is rotated, the cell tissue can be observed from various angles, making it easy to find out a three-dimensional stereoscopic geometry of the cell tissue. Since the cell tissue can be observed under the laser microscope from various angles, it becomes possible to obtain three-dimensional images of the cell tissue that are high in resolution from all of an x-axis direction, a y-axis direction, and a z-axis direction.

Since the window of the first vessel is made from the hydrogel, proteins (having a molecular weight of tens of thousands to hundreds of thousands) and the like necessary for the cultivation can be supplied from a liquid culture medium present outside the first vessel to the culture gel and the cell tissue through the window. This makes it possible to keep the cell tissue activated in the first vessel for long periods of time. This also can prevent the culture gel from swelling by absorbing the liquid culture medium, and can prevent the cell tissue from deviating from its relative position.

The cell culture vessel/the sample cell for observation use according to the present invention can be used in research in, for example, biology, medicine, and pharmacology and can be also used in regenerative medicine, drug development, and so forth.

DESCRIPTION OF EMBODIMENTS

The cell culture vessel/the sample cell for observation use according to the present invention is characterized by being equipped with a culture gel in which a cell or cell tissue is embedded and a first vessel which encloses the culture gel, wherein a space in the first vessel is filled with the culture gel; and the first vessel has a light-permeable window made from a hydrogel.

It is desirable that the window placed in the cell culture vessel/the sample cell for observation use according to the present invention contains an agarose gel, a polyacrylamide gel, a sodium alginate, or a collagen gel.

This makes it possible for the window to have light permeability. This also makes it possible for nourishment such as proteins contained in the liquid culture medium present outside the first vessel to pass through the window, and allows the nourishment to be supplied to the culture gel and the cell tissue. This can also prevent the window from becoming deformed when the first vessel is rotated.

It is desirable that the first vessel, which is configured to be comprised in the cell culture vessel/the sample cell for observation use according to the present invention, is shaped like a rectangular parallelepiped including a cubic shape; and it is desirable that the first vessel has the window at each face.

This makes it possible for the cell tissue inside the first vessel to be observed from six faces on the upper, the lower, the right, the left, the front, and the back sides; and a three-dimensional structure of the three-dimensionally-cultured cell tissue can be perceived. The first vessel can be easily placed on a stage of the microscope, and the cell tissue can be easily observed.

It is desirable that the first vessel, which is configured to be comprised in the cell culture vessel/the sample cell for observation use according to the present invention, has a frame bordering the window.

This can strengthen the first vessel and makes the cell culture vessel/the sample cell for observation use easy to handle. The frame can prevent damage to the window.

It is desirable that the cell culture vessel according to the present invention is also equipped with a second vessel for storing a liquid culture medium, and it is desirable that the first vessel is placed in the liquid culture medium.

This makes it possible for the nourishment such as the proteins contained in the liquid culture medium stored in the second vessel to be supplied to the culture gel and the cell tissue through the window. This makes it possible to maintain activity of the cell tissue in the first vessel for long periods of time. This also makes it possible to take the first vessel easily out of the second vessel, and the outer vessel of the first vessel can be replaced. This makes it possible to replace the outer vessel at the time of cultivation and at the time of observation, and makes it possible to use the outer vessel suitable for each situation.

In the following, one embodiment of the present invention will be described through the use of drawings. Note that compositions indicated in the drawings and the following descriptions are exemplifications and are not to limit the present invention only to the drawings and the following descriptions.

Figure 1:
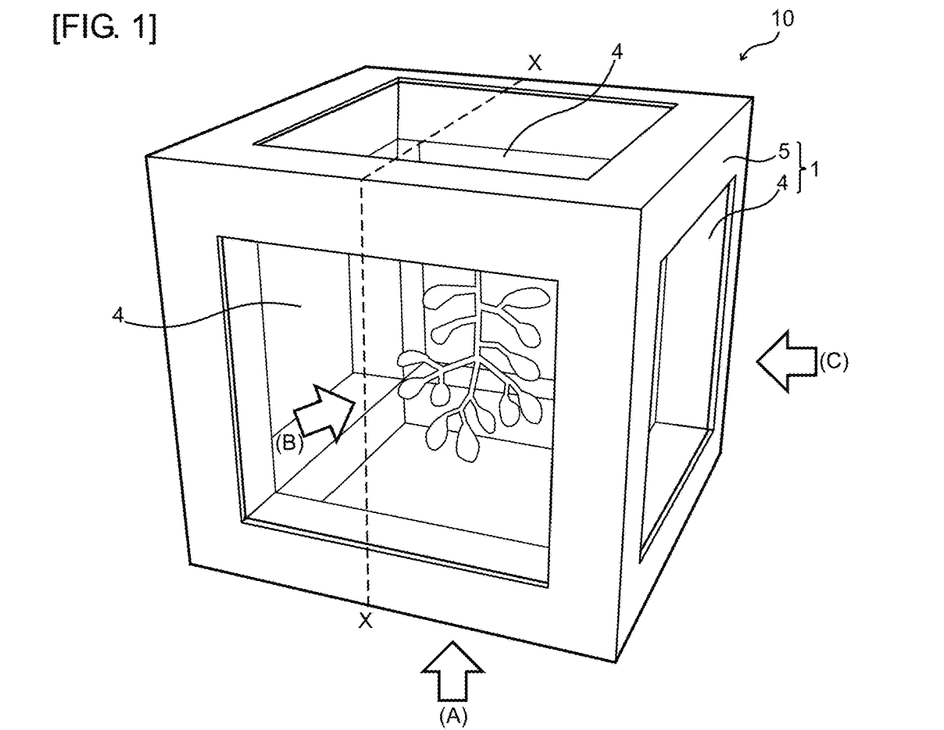
FIG. 1 illustrates a diagrammatic perspective view of a cell culture vessel/a sample cell for observation use in accordance with a first embodiment of the present invention.
Figure 2:
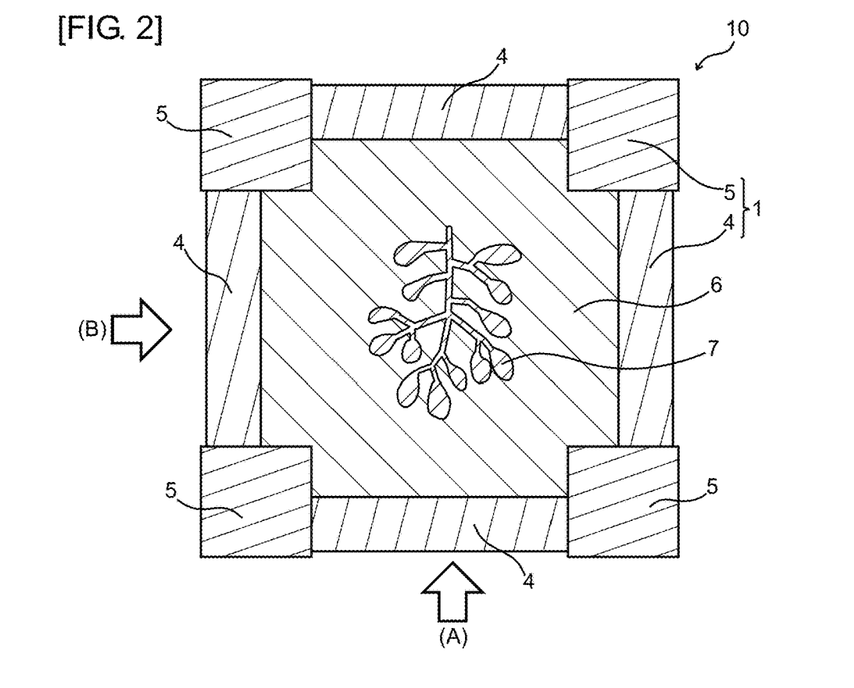
FIG. 2 illustrates a diagrammatic cross-section view of the cell culture vessel/the sample cell for observation use taken along the dashed line X-X of FIG. 1.
Figure 3:
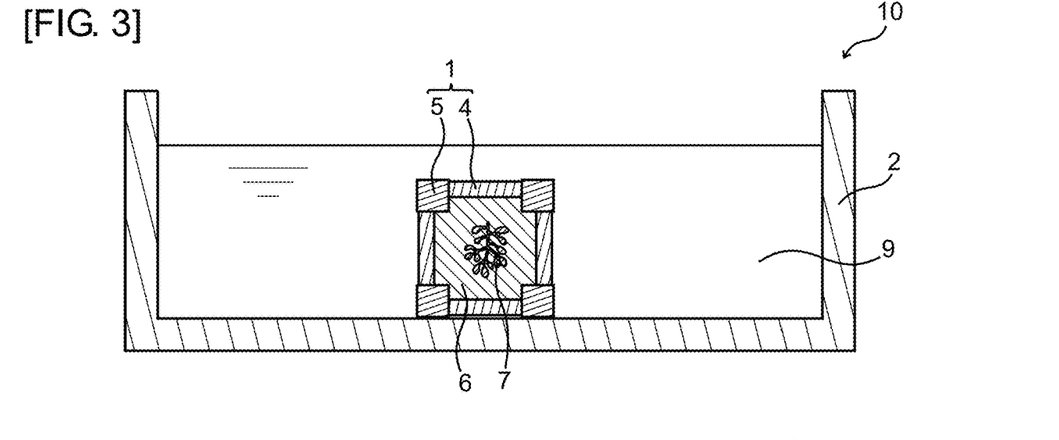
FIG. 3 illustrates a diagrammatic cross-section view of a cell culture vessel in accordance with a second embodiment of the present invention.
Figure 4:
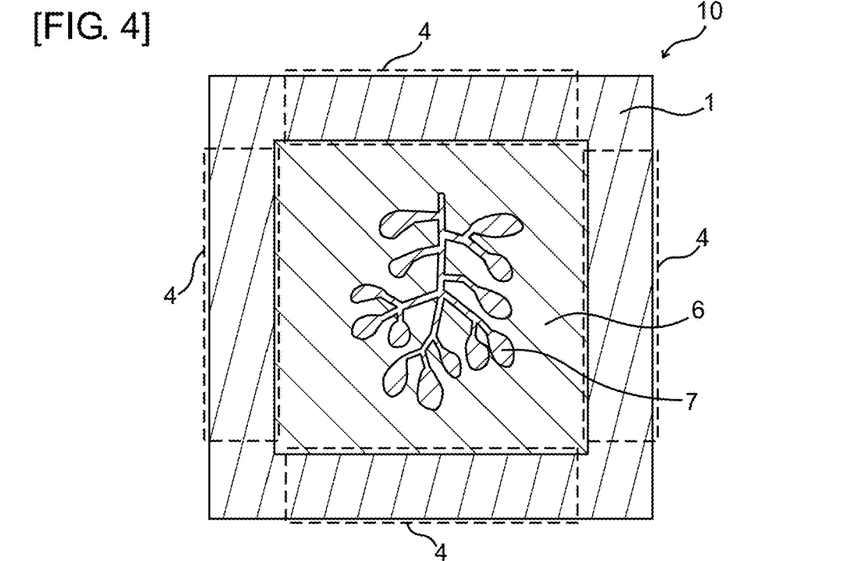
FIG. 4 illustrates a diagrammatic cross-section view of a cell culture vessel/a sample cell for observation use in accordance with a third embodiment of the present invention.

FIG. 1 illustrates a diagrammatic perspective view of a cell culture vessel/a sample cell for observation use in accordance with a first embodiment, and FIG. 2 illustrates a diagrammatic cross-section view of the cell culture vessel/the sample cell for observation use taken along the dashed line X-X of FIG. 1. FIG. 3 illustrates a diagrammatic cross-section view of a cell culture vessel in accordance with a second embodiment. FIG. 4 illustrates a diagrammatic cross-section view of a cell culture vessel/a sample cell for observation use in accordance with a third embodiment. FIGS. 5(a) to 5(c) illustrate diagrammatic perspective views of cell culture vessels/sample cells for observation use in accordance with a fourth embodiment to a sixth embodiment, respectively. It should be noted that a cell culture vessel in accordance with the present embodiment includes the cell culture vessels of the first embodiment to the sixth embodiment.

A cell culture vessel 10/a sample cell for observation use 10 in accordance with the present embodiment is characterized by being equipped with a culture gel 6 in which a cell 7 or cell tissue 7 is embedded and a first vessel 1 which encloses the culture gel 6, wherein a space in the first vessel 1 is filled with the culture gel 6; and the first vessel 1 has a light-permeable window 4 made from a hydrogel.

The cell culture vessel 10 of the present embodiment is to culture the cell tissue in three dimensions. The cell culture vessel 10 of the present embodiment can have functional roles as both a cell culture vessel and a sample cell for observation use.

The culture gel 6 in which the cells 7 or the cell tissue 7 is embedded refers to the culture gel 6 in which the cells 7 or the cell tissue 7 is implanted.

The cell culture vessel 10 of the present embodiment can enclose the cells 7 or the cell tissue 7 embedded in the culture gel. The cell tissue 7 may be living cells, may be tissue fixed with paraformaldehyde or the like, or may be tissue subjected to a permeation treatment.

The cell culture vessel 10 of the present embodiment may have a second vessel 2 in the same way as the cell culture vessel 10 of the second embodiment illustrated in FIG. 3.

The cell culture vessel 10 of the present embodiment may be used as the sample cell for observation use 10. In this case, the cell culture vessel 10 (i.e., the sample cell for observation use) may be set on a stage of a microscope; and the cell tissue 7 cultured in the culture gel 6 can be observed under the microscope. The microscope used for observing the cell tissue 7 may be an optical microscope or a laser microscope.

Figure 10:
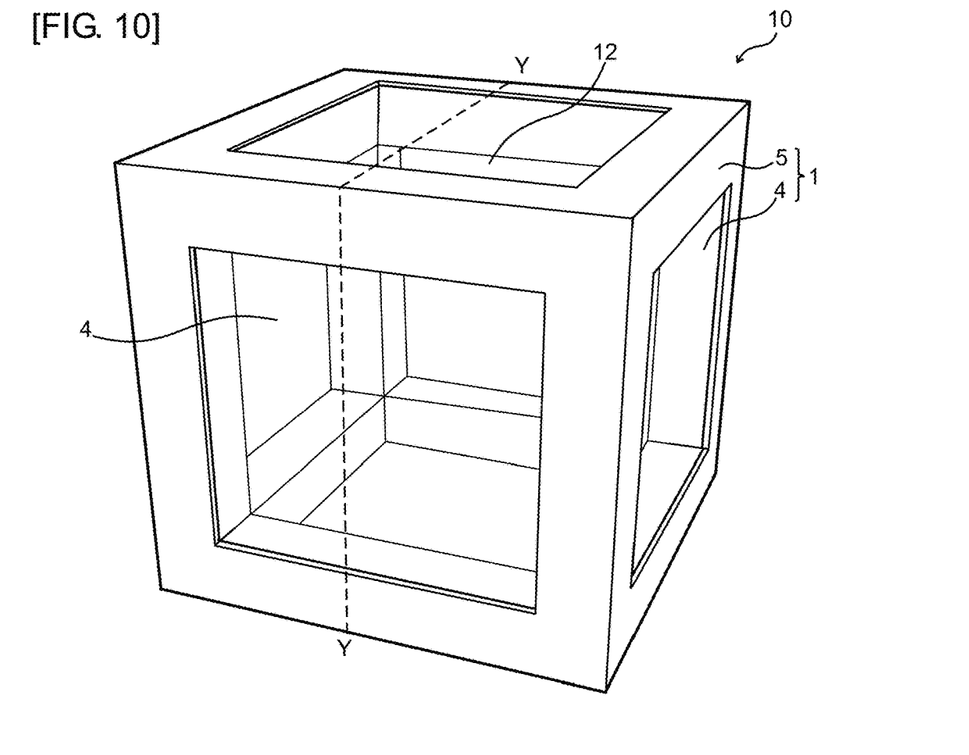
FIG. 10 illustrates a diagrammatic perspective view of a cell culture vessel in accordance with one embodiment of the present invention.
Figure 11:
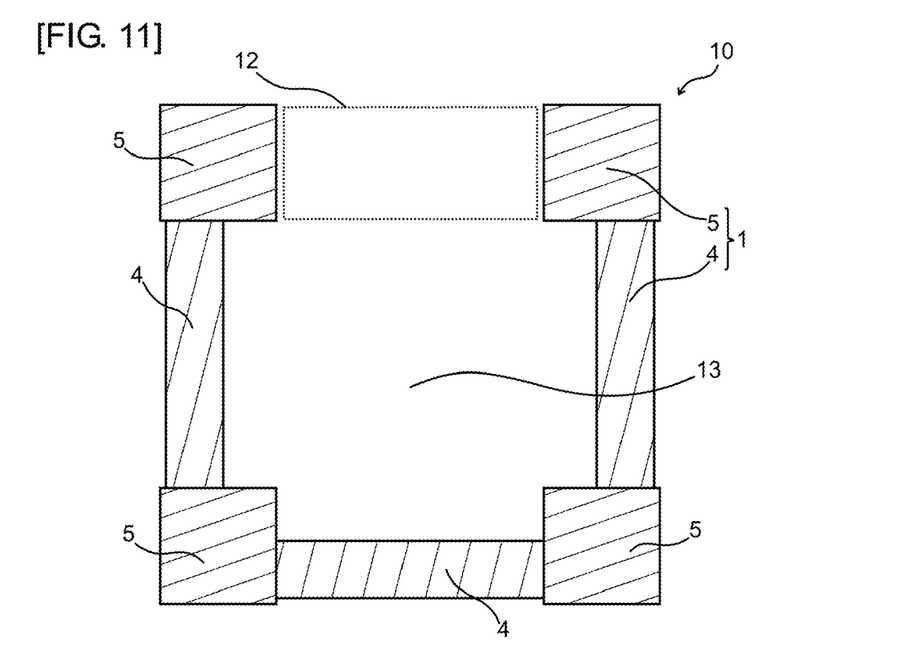
FIG. 11 illustrates a diagrammatic cross-section view of the cell culture vessel taken along the dashed line Y-Y of FIG. 10.

The cell culture vessel 10 of the present embodiment is equipped with the first vessel 1 having an interior space 13 to be filled with the culture gel 6 in which the cells 7 or the cell tissue 7 is embedded, and the first vessel 1 may have the light-permeable window 4 made from the hydrogel. In this case, the cell culture vessel 10 is filled up with the culture gel 6 with the cells 7 or the cell tissue 7; and then the cells 7 or the cell tissue 7 can be cultured and observed. This cell culture vessel 10 may also have an opening 12 used for injecting the culture gel 6, etc. into the interior space 13 of the first vessel 1. After the culture gel 6, etc. is injected into the interior space 13 of the first vessel 1, the light-permeable window 4 made from the hydrogel may be formed at this opening 12. The cell culture vessel 10 may have a structure, for example, as illustrated in FIGS. 10 and 11.

In the following, the cell culture vessel 10/the sample cell for observation use 10 of the present embodiment will be described.

1. Culture Gel

The culture gel 6 is to culture the cells 7 or the cell tissue 7 embedded therein. The cells to be embedded in the culture gel 6 may be cell tissue having a structure where the cells aggregate in a specific pattern, or may be cells that do not have such a tissue structure. The cells 7 without having the tissue structure may be cultured to grow into cell tissue 7.

The cells 7 or the cell tissue 7 embedded in the culture gel 6 can be supplied with the nourishment through the culture gel 6. The culture gel 6 can function as a scaffold for the cell tissue 7, and can allow the cell tissue 7 to grow in three dimensions.

The culture gel 6 can contain, for example, any of collagen, laminin, entactin, and proteoglycan. The culture gel 6 can also contain, for example, any of a TGF-β, a fibroblast growth factor, and a tissue plasminogen activator. Used as the culture gel 6 is, for example, Matrigel™.

Since the culture gel 6 is enclosed in the first vessel 1 and is not directly in contact with a liquid culture medium present outside the first vessel, the culture gel 6 can be prevented from swelling by absorbing the liquid culture medium; and the cell tissue 7 is prevented from deviating from its relative position.

2. First Vessel

The first vessel 1 is configured to enclose the culture gel 6. The space in the first vessel 1 is filled with the culture gel 6 in which the cell tissue 7 is embedded. This makes it possible to confine the culture gel 6 and the cell tissue 7 in the first vessel 1, and can prevent the culture gel 6 from moving inside (or drifting in) the first vessel 1 and can also prevent the cell tissue 7 from deviating from its relative position. Because the relative position of the cell tissue 7 is prevented from shifting, the first vessel 1 is capable of being rotated in a horizontal direction, a vertical direction, or an oblique direction. Because of being stored in the first vessel 1, the culture gel 6, in which the cell tissue 7 is embedded, can be easily handled. This makes it easy to replace an outer vessel that stores (holds) the first vessel 1. For example, in a case where a plastic well plate having many wells is used—each well may store (hold) one first vessel 1 therein—and cell tissue 7 is cultured in each first vessel 1. To obtain fluorescence images, etc. of the cell tissue 7, first vessels 1 may be taken out of the well plate and may be placed in another outer vessel having a glass undersurface that is high in light permeability. This makes it possible to obtain the clear fluorescence images, etc. of the cell tissue 7. The plastic well plate is not suited for obtaining fluorescence images because of its poor light permeability. After the fluorescence images are photographed, the first vessel 1 may be returned to the well plate.

The first vessel 1 may have strength in such a way as not to deform its shape even when the first vessel 1 is rotated. The first vessel 1 may also have a sealed structure, and its interior space may be filled with the culture gel 6 and the cell tissue 7.

The first vessel 1 may be, for example, polyhedral in shape. This allows the first vessel 1 to have a base surface, and thus makes it possible to specify an observation surface for observing the cell tissue 7. This makes it possible to set a coordinate system for identifying a three-dimensional structure of the cell tissue 7. For example, to set three-dimensional orthogonal coordinate, one plane surface of the polyhedron may be set as a base surface; and X-Y coordinate may be set in this plane surface; and then a Z-coordinate may be set along a line perpendicular to the above-mentioned plane surface. In a case where a polyhedron has three plane surfaces that are perpendicular to each other, a three-dimensional orthogonal coordinate system may be set based on these three plane surfaces as base surfaces.

Figure 5:
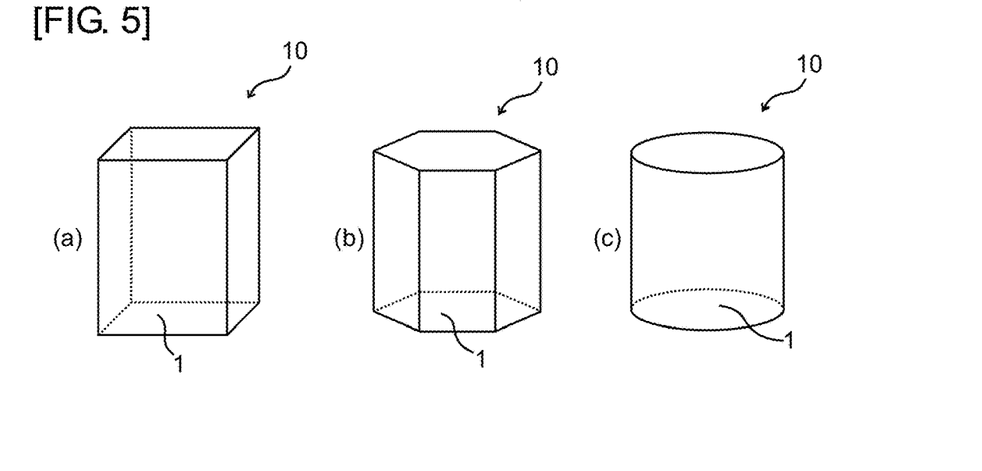
FIGS. 5(a) to 5(c) illustrate diagrammatic perspective views of cell culture vessels/sample cells for observation use in accordance with a fourth embodiment to a sixth embodiment of the present invention, respectively.

The first vessel 1 may have a cubic shape as illustrated in FIGS. 1 to 4, may be shaped like a rectangular parallelepiped as illustrated in FIG. 5(*a*), or may be shaped like a hexagonal column as illustrated in FIG. 5(*b*). The first vessel 1 may also be shaped like a circular cylinder as illustrated in FIG. 5(*c*).

Also, the first vessel 1 may be tetrahedral in shape (three-sided pyramid) or pentahedral (triangle pole, four-sided pyramid, etc.), or may be hexahedral in shape besides the rectangular parallelepiped (parallelepipedon, triangular bipyramid, etc.), heptahedral (pentagonal column, six-sided pyramid, etc.), or octahedral (square bipyramid, etc.). The first vessel may also be decahedral in shape (pentagonal bipyramid, etc.) or dodecahedral (regular dodecahedron, rhombic dodecahedron, cubdodecahedron, etc.). The first vessel 1 may have more faces (; however, the number of the faces should not be too many in order to secure a wide area of each window 4; and the first vessel is preferably tetrahedral, pentahedral, hexahedral, heptahedral, or octahedral in shape. The first vessel in the shape of the hexahedron is particularly suited for three-dimensional observation because this first vessel has large windows in three directions.

The first vessel 1 can be sized in such a way that each side of the vessel is, for example, 1 mm or longer to 5 cm or shorter in length. The first vessel 1 may be, for example, 1 μL or higher to 10 mL or lower in volume.

The first vessel 1 has the light-permeable window 4. This allows the cell tissue 7 inside the first vessel 1 to be observed under the microscope or the like through the window 4. In the case where the first vessel 1 is polyhedral in shape as illustrated in FIGS. 1 to 4, 5(*a*) and 5(*b*), the window 4 may be placed at each face of the first vessel 1. This makes it possible for the cell tissue 7 inside the first vessel 1 to be observed from each face of the first vessel 1. As illustrated in FIGS. 1 to 4, the window 4 may be placed, for example, at each face of the first vessel 1. To observe the cell tissue 7 through the windows 4, the first vessel 1 may be placed in a glass vessel that is high in light permeability. This can prevent the liquid culture medium, etc. to adhere to the microscope.

The window 4 may be, for example, in the form of a film. The window 4 may also be in the form of a plate. The window 4 may be thick; however, the window 4 configured to be thin such as the film-like form or the plate-like form can improve its light permeability and protein permeability.

The first vessel 1 can be rotated in such a way as to prevent the cell tissue 7 from deviating from its relative position, and thus can be rotated in such a way that each face of the first vessel 1 where the window 4 is placed can function as the observation surface of the sample cell for observation use 10. It makes it particularly possible to turn over an upper surface and a lower surface of the first vessel 1 and to turn over the first vessel 1 sideways. Such rotations allow the cell tissue 7 inside the first vessel 1 to be observed from each face, and make it easy to find out a three-dimensional stereoscopic geometry of the cell tissue 7. The microscope used for observing the cell tissue 7 may be an optical microscope or a laser microscope.

In the case where the first vessel 1 is shaped like the circular cylinder as illustrated in FIG. 5(c), the window 4 can be placed at a side surface of the circular cylinder. This makes it possible to obtain three-dimensional images of the cell tissue 7 by using the laser microscope. The window 4 may also be placed at an upper surface and a lower surface of the circular cylinder. This makes it possible for the cell tissue 7 to be observed from both the upper surface and the lower surface, and can improve resolution of the three-dimensional images.

The window 4 of the first vessel 1 is made from the hydrogel. This makes it possible to supply proteins (having a molecular weight of tens of thousands to hundreds of thousands) and the like necessary for the cultivation from the liquid culture medium, etc. present outside the first vessel 1 to the culture gel 6 and the cell tissue 7 through the window 4. The cell culture vessel 10 may be equipped with the second vessel 2 for storing a liquid culture medium 9, and is configured to place the first vessel 1 in the liquid culture medium 9. For example, the cell culture vessel 10 may be equipped with the second vessel 2 as illustrated in FIG. 3 referring to the second embodiment. This makes it possible to supply the nourishment such as the proteins contained in the liquid culture medium 9 stored in the second vessel 2 to the culture gel 6 and the cell tissue 7 through the window 4. This makes it possible to keep the cell tissue 7 activated in the first vessel 1 for long periods of time. Since the culture gel 6 is not directly in contact with the liquid culture medium 9, the culture gel 6 can be prevented from swelling by absorbing the liquid culture medium 9; and the cell tissue 7 is prevented from deviating from its relative position. For example, the second vessel 2 may be a well plate having some wells. This allows the wells to respectively store (hold) some first vessels 1 therein and thus can culture many cell tissues 7.

The liquid culture medium 9 stored in the second vessel 2 may be freshened periodically. The cell culture vessel 10 may be equipped with a third vessel that stores another liquid culture medium. The first vessel 1, which is set in the second vessel 2, may culture the cell tissue for a certain period of time; and then the first vessel 1 may be taken out of the second vessel 2 to be immersed in the liquid culture medium stored in the third vessel. The second vessel 2 may be equipped with some wells. The cell tissue 7 may be cultured in the first vessel 1 placed in one of the wells, and then the first vessel 1 may be taken out of the well to be placed in another well. This can prevent the first vessel 1 from being kept in the liquid culture medium low in nourishing materials, and makes it possible to maintain activity of the cell tissue 7 for long periods of time.

The hydrogel that forms the window 4 is not particularly limited, as long as the hydrogel allows the proteins to pass therethrough and has enough hardness to keep itself sustained. The hydrogel is formed by linking dispersoid in water and forming a network, and becomes a solid form in its whole system.

The strength and the protein permeability of the window 4 can be adjusted by adjusting a concentration of the dispersoid forming the network of the hydrogel used as the window 4.

The higher the concentration of the dispersoid forming the network is, the higher the strength of the window 4 is. It is desirable that the window 4 has the gel strength of 50 g/cm$^2$ or higher, and this can prevent the window 4 from being deformed by a weight of the culture gel 6 inside the first vessel 1.

An overly high concentration of the dispersoid causes a decrease in the protein permeability; therefore, to secure the protein permeability, it is desirable that the concentration of the dispersoid is controlled (or adjusted) in such a way that the window 4 has the strength of 10,000 g/cm$^2$ or lower.

It is thus preferable that the window 4 has the strength of 50 g/cm$^2$ or higher to 10,000 g/cm$^2$ or lower. An adequate concentration of the dispersoid in order to obtain the gel strength such as the one above varies depending on the kind of the dispersoid.

The window 4 may contain, for example, an agarose gel, a polyacrylamide gel, a sodium alginate, or a collagen gel. This makes it possible for the window 4 to have the light permeability. This also makes it possible for the nourishment such as the proteins contained in the liquid culture medium 9 stored in the second vessel 2 to pass through the window 4, and makes it possible for the nourishment to be supplied to the culture gel 6 and the cell tissue 7. The window 4 can be prevented from being deformed while the first vessel 1 is rotated because the window 4 contains the agarose gel, the polyacrylamide gel, the sodium alginate, or the collagen gel. Preferably, the window 4 is made from the agarose gel or the polyacrylamide gel. This makes it easy to adjust the hardness of the window 4. This can also reduce production costs of the cell culture vessel 10.

In the case where the window 4 is made from the agarose gel, a concentration of agarose may be, for example, 0.5 to 4.0%. In the case where the window 4 is made from the polyacrylamide gel, a concentration of polyacrylamide may be, for example, 3 to 20%. To form the sodium alginate-containing window 4, calcium ions are added to a sodium alginate solution so as to gelatinize the solution. To form the collagen gel-containing window 4, the collagen gel should be high in concentration. This makes it possible for the window 4 to have adequate strength.

The first vessel 1 may have a frame 5 bordering each window 4. This can strengthen the first vessel 1 and makes the cell culture vessel 10/the sample cell for observation use 10 easy to handle. The frame can prevent damage to the window 4. As illustrated in FIGS. 1 to 3, for example, the first vessel 1 may be constructed from the frame 5 and the windows 4. The frame 5 may be made from a biocompatible resin. Used as the material of the frame 5 is, for example, a polycarbonate.

The cell culture vessel 10/the sample cell for observation use 10 as illustrated in FIGS. 1 and 2 may be manufactured as follows. Set a frame 5 in a cubic form having openings on six faces, respectively; pour a sol for forming window 4 into the opening bordered by the frame 5; and gelatinize the sol to form film-like or sheet-like window 5 made from the hydrogel. In this way, a window 5 is formed at each of the five surfaces bordered by the frame 5; after that, a yet-to-be-gelatinized culture gel and cell tissue are injected into the frame 5 in the cubic form; and then the culture gel is gelatinized. Then the sol for forming window 4 is poured into one remaining opening bordered by the frame 5 and is gelatinized to form a film-like or sheet-like window 4. As described above, the first vessel 1 can be manufactured that encloses the cell tissue 7 and the culture gel 6.

The first vessel 1 may not have any frame 5 and may be constructed from the hydrogel forming the window 4. This can prevent any blind spots that get in the way of observing the cell tissue through the window 4. Especially in the case where the first vessel 1 is too small in size (for example, 5 mm or shorter on a side), the first vessel 1 can be constructed without having any frame 5. For example, as illustrated in FIG. 4, the first vessel 1 may not have any frame 5.

The cell culture vessel 10/the sample cell for observation use 10 as illustrated in FIG. 4 may be manufactured as follows. Pour a sol for forming window 4 into a mold; gelatinize the sol; and form a hollow cubic gel having one opening at one surface of the cubic gel. After that, a yet-to-be-gelatinized culture gel and cell tissue are injected into the cubic gel; and then the culture gel is gelatinized. Then the sol for forming window 4 is poured into the opening of the cubic gel and is gelatinized to form a window 5. As described above, the first vessel 1 can be manufactured that encloses the cell tissue 7 and the culture gel 6.

Cell Culture Experiments and Cell Observation Experiments

A first vessel enclosing bronchial tissue, as illustrated in FIGS. 1 and 2, was manufactured; and the first vessel was placed in a liquid culture medium, as illustrated in FIG. 3, so as to culture the bronchial tissue. Firstly, a polycarbonate frame in a cubic form was prepared, 1 cm on a side; and windows were formed by using a 1.5% agarose gel. After that, Matrigel™ as a culture gel and bronchial tissue were injected into the cube; and the culture gel was gelatinized; and then a window was formed at a remaining opening by using the 1.5% agarose gel. In this way, the first vessel was manufactured. This first vessel was placed in a liquid culture medium, and the bronchial tissue was three-dimensionally cultured for ten (10) days. Then the cultured bronchial tissue was observed under an optical microscope.

During the cell culture experiment, any swelling of the culture gel and any decrease in cell activity were not observed in the first vessel.

Figure 6:
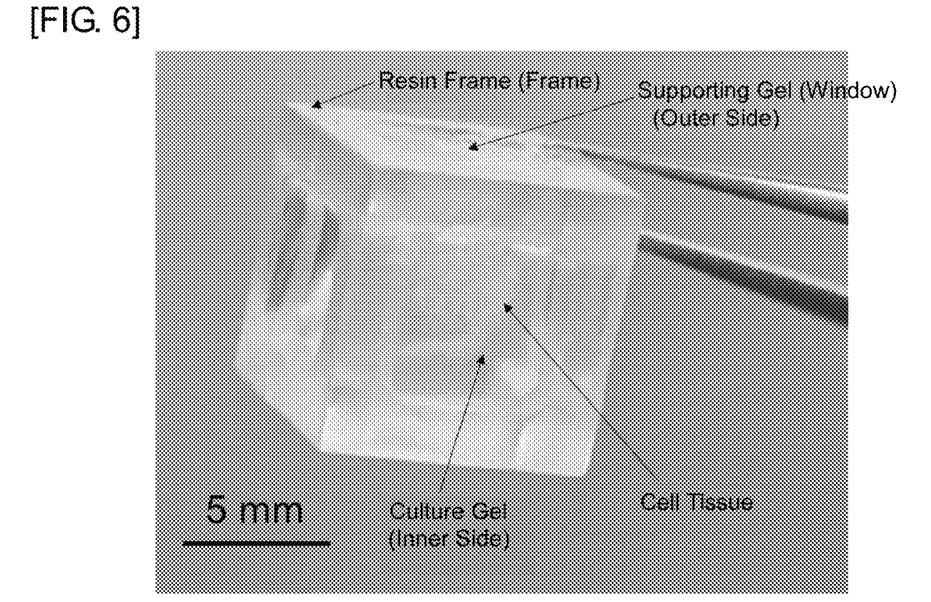
FIG. 6 shows a photograph of a cell culture vessel/a sample cell for observation use manufactured by an experiment.
Figure 7:
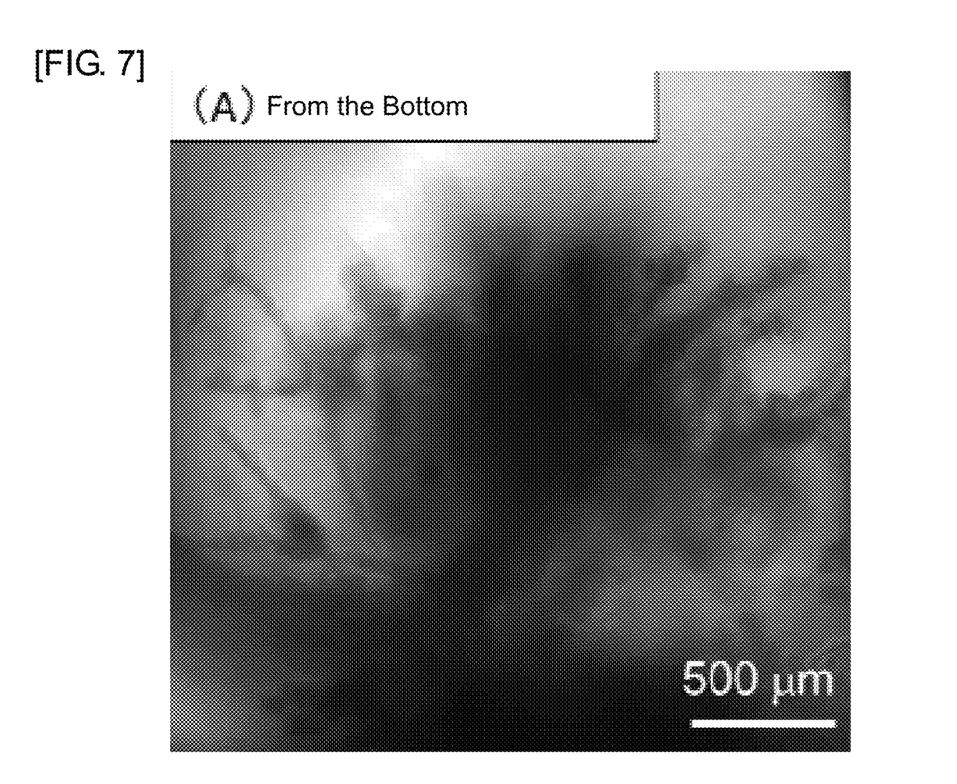
FIG. 7 shows a photograph of cell tissue photographed from a lower face of the cell culture vessel/the sample cell for observation use manufactured by the experiment.
Figure 8:
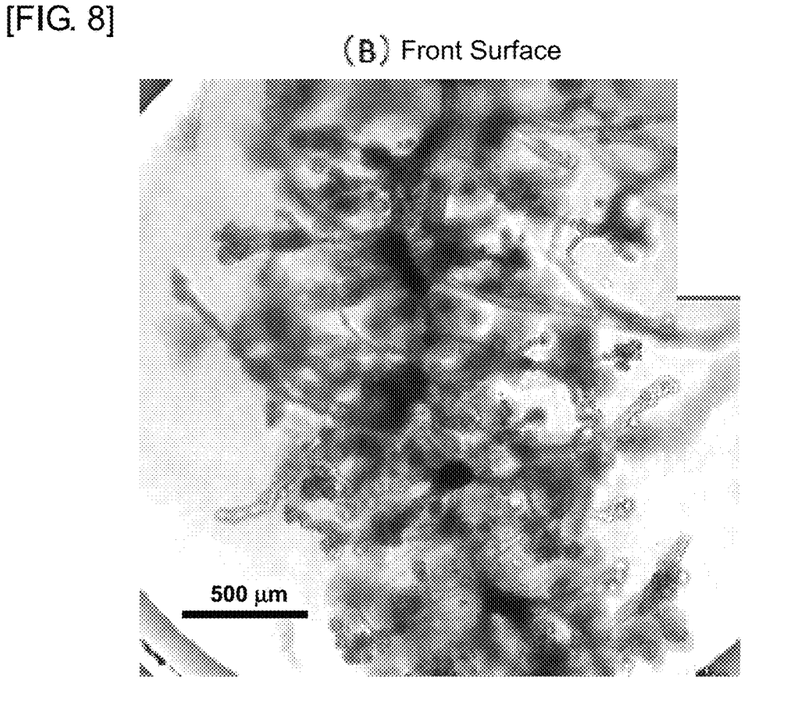
FIG. 8 shows a photograph of the cell tissue photographed from a front face of the cell culture vessel/the sample cell for observation use manufactured by the experiment.

FIG. 6 shows a photograph of the first vessel after the cultivation. FIG. 7 shows a photograph in which the bronchial tissue was photographed through the window at a lower surface of the first vessel (i.e., photographed from a direction (A) indicated in FIGS. 1 and 2); FIG. 8 shows a photograph in which the bronchial tissue was photographed through the window at a front surface of the first vessel (i.e., photographed from a direction (B) indicated in FIGS. 1 and 2); and FIG. 9 shows a photograph in which the bronchial tissue was photographed through the window at a right surface of the first vessel (i.e., photographed from a direction (C) indicated in FIGS. 1 and 2).

In the photograph of FIG. 7 taken through the window at the lower surface, a central portion of the bronchial tissue became dark. Reason for this was that the bronchial tissue grew in a vertical direction, and light irradiated on the sample cell could not pass through the bronchial tissue. From the photograph of FIG. 7, a two-dimensional geometry of the bronchial tissue was perceived that grew in a lateral direction from its central portion. Also, from another photograph taken through the window at an upper surface of the first vessel (though this photograph is not shown), a two-dimensional geometry of the bronchial tissue was perceived that grew in a lateral direction from its central portion.

Figure 9:
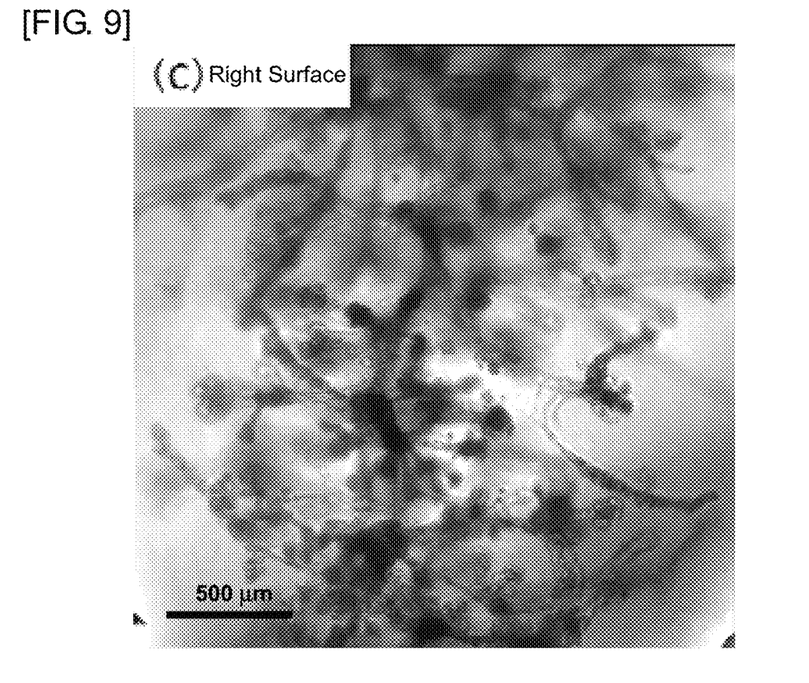
FIG. 9 shows a photograph of the cell tissue photographed from a right face of the cell culture vessel/the sample cell for observation use manufactured by the experiment.

From the photograph of FIG. 8 taken through the window at the front surface and the photograph of FIG. 9 taken through the window at the right surface, two-dimensional geometries of the bronchial tissue were perceived that grew in a vertical direction. Also, from a photograph taken through the window at a back surface of the first vessel and a photograph taken through the window at a left surface of the first vessel (though these photographs are not shown), two-dimensional geometries of the bronchial tissue were perceived.

By multi-view matching the two-dimensional images of the bronchial tissue observed through all the windows, a three-dimensional structure of the three-dimensionally-cultured bronchial tissue can be perceived.

REFERENCE SIGNS LIST

1 First vessel
2 Second vessel
4 Window
5 Frame
6 Culture gel
7 Cell tissue (cells)
9 Liquid culture medium
10 Cell culture vessel or sample cell for observation use
12 Opening
13 Interior space

The invention claimed is:

1. A cell culture vessel comprising a culture gel in which a cell or cell tissue is embedded and a first vessel which encloses the culture gel, wherein
　a space in the first vessel is filled with the culture gel,
　the first vessel is cubical in shape or cuboid in shape, and the first vessel has a single window made from a hydrogel at each face, the windows being light-permeable,
　the windows are arranged in such a way that the cell or the cell tissue is observed from all of the faces for perceiving the three-dimensional structure of the cell or the cell tissue, and
　the first vessel has a frame bordering the windows.

2. The cell culture vessel according to claim 1, wherein the windows comprise an agarose gel, a polyacrylamide gel, a sodium alginate, or a collagen gel.

3. The cell culture vessel according to claim 1, wherein the windows have a gel strength of 50 g/cm$^2$ or higher to 10,000 g/cm$^2$ or lower.

4. The cell culture vessel according to claim 1, further comprising a second vessel for storing a liquid culture medium, wherein the first vessel is placed in the liquid culture medium.

5. A sample cell for observation use comprising a culture gel in which a cell or cell tissue is embedded and a first vessel which encloses the culture gel, wherein
　a space in the first vessel is filled with the culture gel,
　the first vessel is cubical in shape or cuboid in shape, and the first vessel has a single window made from a hydrogel at each face, the windows being light-permeable, the windows are arranged in such a way that the cell or the cell tissue is observed from all of the faces for perceiving the three-dimensional structure of the cell or the cell tissue, and the first vessel has a frame bordering the windows.

6. A cell culture vessel comprising a first vessel having an interior space to be filled with a culture gel in which a cell or cell tissue is embedded, wherein the first vessel is cubical in shape or cuboid in shape, and the first vessel has a single window made from a hydrogel at each face, the windows being light-permeable, the windows are arranged in such a way that the cell or the cell tissue is observed from all of the faces for perceiving the three-dimensional structure of the cell or the cell tissue, and the first vessel has a frame bordering the windows.

7. A method for producing a cell culture vessel, comprising the step of filling up an interior space of a first vessel with a culture gel and a cell or the culture gel and cell tissue via an opening, wherein the first vessel is cubical in shape or cuboid in shape, and the first vessel has the opening at one face and a single window made from a hydrogel at each of the other faces, the windows are light-permeable and arranged in such a way that the cell or the cell tissue is observed from the faces for perceiving the three-dimensional structure of the cell or the cell tissue, and the first vessel has a frame bordering the windows.

8. The method according to claim 7, further comprising the step of forming a light-permeable window made from a hydrogel in the opening after the step of filling up the interior space with the culture gel and the cell, or the culture gel and the cell tissue.

* * * * *